United States Patent [19]

Duerr

[11] Patent Number: 5,699,802
[45] Date of Patent: Dec. 23, 1997

[54] MAMMOGRAPHY ANTENNA ARRANGEMENT FOR NMR EXAMINATIONS OF A FEMALE BREAST

[75] Inventor: Wilhelm Duerr, Erlangen, Germany

[73] Assignee: Siemens Aktiengesellschaft, Munich, Germany

[21] Appl. No.: 536,950

[22] Filed: Sep. 29, 1995

[30] Foreign Application Priority Data

Sep. 29, 1994 [DE] Germany .................. 44 34 949.1

[51] Int. Cl.$^6$ .................................................. A61B 5/055
[52] U.S. Cl. ...................... 128/653.5; 324/318; 324/322
[58] Field of Search ..................... 128/653.2, 653.5; 324/318, 322

[56] References Cited

U.S. PATENT DOCUMENTS

| | | |
|---|---|---|
| 4,467,282 | 8/1984 | Siebold . |
| 4,680,549 | 7/1987 | Tanttu . |
| 4,691,163 | 9/1987 | Blass et al. . |
| 5,280,249 | 1/1994 | Kess . |
| 5,293,519 | 3/1994 | Yoshino et al. . |
| 5,317,266 | 5/1994 | Meissner . |
| 5,363,845 | 11/1994 | Chowdhury et al. ............. 128/653.5 |

FOREIGN PATENT DOCUMENTS 0 565 178  10/1993  European Pat. Off. .

OTHER PUBLICATIONS

"A Novel Multi-Segment Tansmit-Receive Coil for Neuro Functional MR Imaging," Lin et al. SMRM, Aug., 1994 p. 1105.

*Primary Examiner*—Ruth S. Smith
*Attorney, Agent, or Firm*—Hill, Steadman & Simpson

[57] ABSTRACT

In a mammography antenna arrangement for magnetic resonance examinations of a female breast, a conductor arrangement forms a closed circuit and surrounds a receptacle opening for the female breast. The receptacle opening lies in a surface that is essentially horizontally directed. Two arcuate conductor segments have their ends connected to the conductor arrangement via electrical connecting locations and surround an examination space that is fashioned for the acceptance of the female breast. The two conductor segments are respectively arranged in vertical, planes, the two planes being perpendicular to one another.

20 Claims, 3 Drawing Sheets

MAMMOGRAPHY ANTENNA ARRANGEMENT FOR NMR EXAMINATIONS OF A FEMALE BREAST

BACKGROUND OF THE INVENTION

1. Field of the Invention

The present invention is directed to an antenna arrangement specifically adapted for conducting a nuclear magnetic resonance examination of a female breast.

2. Description of the Prior Art

An antenna arrangement of the species initially cited is known from the conference volume of the SMRM Congress, August 1994 in the USA, page 1105, by Chin-S. Lin, Jonathan Gold and Sunder Rajan, "A Novel Multi-Segment Transmit-Receive Coil for Neuro Functional MR Imaging". This known antenna arrangement used a baseball helmet as a basis for the coil construction. The antenna includes first and second arcuate conductors respectively disposed in different planes, the planes being perpendicular to each other. Each arcuate conductor has a zenith at which signals are supplied to and tapped from the conductor. The free ends of both arcuate conductors are connected to a further conductor. Each segment of each arcuate conductor between its zenith and the node at which it is connected to the further conductor contains a capacitor. Moreover, the further conductor is divided into four segments, between the respective connection points with the arcuate conductors. Each segment of the further conductor also contains a capacitor. This antenna arrangement is operated in one of three different modes that are obtainable due to the different possible current paths in the antenna arrangement when a signal terminal is arranged at the zenith of the arcuate conductor segments. Compared to a conventional, circularly polarizing head antenna, the antenna described therein supplies signals with a higher signal-to-noise ratio. Employment of this known antenna for MR imaging of the female breast, however, is not proposed therein.

U.S. Pat. No. 5,280,249 discloses an antenna arrangement for examining a female breast. The antenna arrangement disclosed therein has two sub-antennas decoupled from one another for generating or for receiving circularly polarized radio-frequency fields. The first sub-antenna is designed as a frame coil and surrounds a receptacle opening for the breast to be examined. The second sub-antenna has two sub-coils that are arranged opposite one another and are penetrated by the frame coil. The circularly polarizing field characteristic is present in an examination space disposed inside the frame coil and outside the sub-coils. Utilization of the antenna arrangement in a magnetic resonance apparatus ensues with the static main or basic magnetic field proceeding parallel to an imaginary connecting line between the two sub-coils. Given a horizontal alignment of the main magnetic field, the receptacle opening thereby lies in a horizontal plane. Breast examinations can then be implemented with the patient in a prone position. For employment of this antenna arrangement in magnetic resonance apparatus having a vertically aligned main magnetic field, the receptacle opening then likewise lies in a surface that is essentially vertically directed.

An antenna arrangement with a circularly polarizing field characteristic that is provided for examining the head is also known. This antenna arrangement has four strip-shaped conductor segments directed axially on a cylindrical jacket. Neighboring conductor segments are connected to one another at their ends via respective capacitors. The antenna arrangement is provided for use in a magnetic resonance apparatus of the type having a horizontally aligned basic magnetic field, and the conductor segments must be aligned parallel to the basic magnetic field. The antenna arrangement could fundamentally also be employed in magnetic resonance systems having a vertical magnetic field, whereby the receptacle opening would come to lie in an essentially horizontal surface. The antenna arrangement is less suited, however, for magnetic resonance mammography because the structure of such an antenna is poorly matched to the anatomy of the female breast and the optimum image quality is thus not achieved.

SUMMARY OF THE INVENTION

An object of the present invention is to provide an antenna arrangement with which, given a vertically directed basic magnetic field, magnetic resonance examinations of the female breast with the patient in a prone position can be implemented with high image quality.

The above object is achieved in accordance with the principles of the present invention in an antenna arrangement formed by two arcuate conductors, each disposed in a separate plane, with the planes being perpendicular to each other, and the free ends of the arcuate conductors all being connected by a further conductor. In one embodiment, the four segments of the further conductor defined by the respective junctions with the arcuate conductors each contain a capacitor and a first signal terminal is connected across a first of these capacitors, and a second signal terminal is connected across a second of these capacitors, the first and second capacitors being neighboring, i.e., being connected to a common junction. In a second embodiment, each of the arcuate conductors contains a capacitor between the junction with the further conductor and the zenith of the arcuate conductor. In this embodiment, a first signal terminal is connected across a first of these capacitors and a second signal terminal is connected across a second of these capacitors.

The arcuate conductor segments allow a good geometrical matching of the antenna arrangement to the region under examination, even in a region of the examination space remote from the receptacle opening, a high signal-to-noise ratio being achieved as a result. As a result of the relatively open design of the antenna system, systems for fixing the breast as well as localization means for lesions or biopsy systems can be well-accommodated. An array mode via the signal terminals as well as the generation and reception of circularly polarizing fields are possible.

In an embodiment of the invention, the two conductor segments are fashioned alike and are respectively fashioned symmetrical relative to a symmetry axis, with the symmetry axes coinciding. The two sub-systems are thus already decoupled from one another as a result of the symmetry.

In a further embodiment, the two conductor segments are fashioned ribbon-like for optimizing the field homogeneity.

In an especially advantageous embodiment the conductor arrangement has a distended portion. An adequate sensitivity of the antenna arrangement for horizontal field components can thus also be achieved in the diagnostically interesting lymph discharge region of the breast in the area of the axilla. A decoupling of the asymmetrical antenna arrangement can be achieved with a suitable selection of the capacitative elements, and possibly additional inductances.

In another embodiment, a further conductor loop is arranged laterally from the receptacle opening and facing away from the examination space in order to likewise enhance the sensitivity in the area of the axilla.

A further embodiment is directed to an antenna system having two identical antenna arrangements arranged side-by-side and identically directed, whereby a radio-frequency shield is arranged between the two antenna arrangements. The radio-frequency shield serves the purpose of decoupling the two individual systems that would otherwise be disrupted in their symmetry due to their close proximity. The radio-frequency shield can be made slotted in order to avoid gradient eddy currents.

DESCRIPTION OF THE PREFERRED EMBODIMENTS

Figure 1:
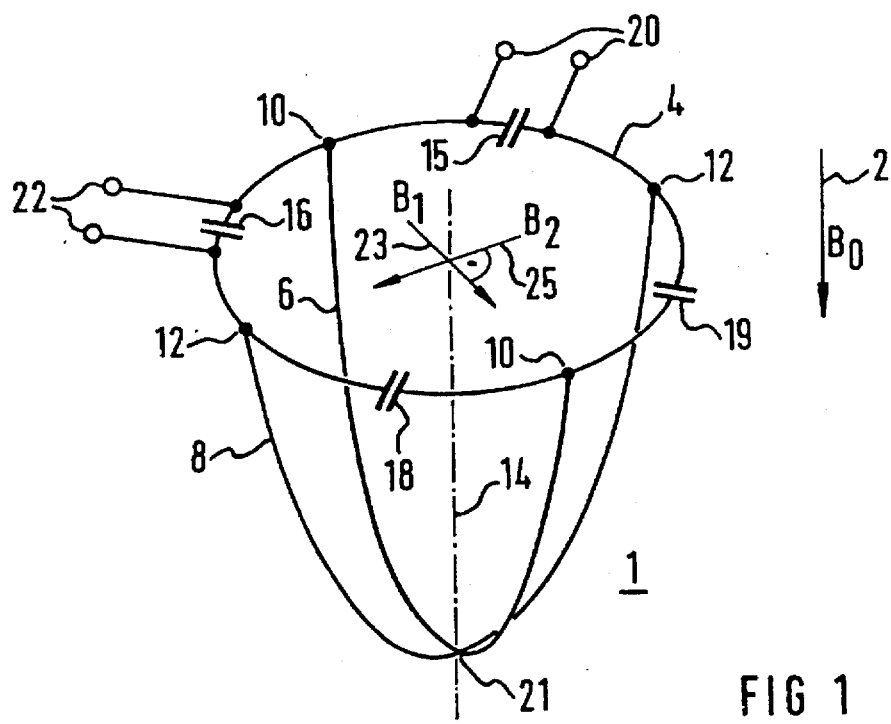
FIG. 1 illustrates a basic mammography antenna arrangement constructed in accordance with the principles of the present invention for use in a magnetic resonance apparatus with a vertical basic magnetic field.

The mammography antenna arrangement 1 shown in perspective in FIG. 1 is provided for use in a magnetic resonance apparatus with a vertical basic field $B_o$. The vertical magnetic field direction is symbolized by an arrow 2. A circular, closed conductor arrangement 4 is arranged in a horizontal plane. It surrounds a receptacle opening for the female breast, so that an examination can be implemented with the patient in a prone position. Two arcuate conductor segments 6 and 8 have their ends connected to the conductor arrangement 4 via respective electrical junctions 10 and 12. The two conductor segments 6 and 8 are arranged in respective vertical planes, the two planes being perpendicular to one another.

The two conductor segments 6 and 8 are identical and are each fashioned symmetrically relative to a symmetry axis 14. The symmetry axes 14 coincide and proceed through the middle point of the circular conductor arrangement 4. Given this completely symmetrical arrangement of the conductor segments 6 and 8, the connecting points 10 and 12 respectively lie on a line through the middle point of the circular conductor arrangement 4, the two lines intersecting at a right angle.

The conductor segments 6 and 8 surround an examination space that in the exemplary embodiment is fashioned for the acceptance of an average female breast.

Capacitive elements 15, 16, 18 and 19 are respectively inserted between two neighboring connecting points 10 and 12 in the conductor arrangement for tuning the antenna arrangement 1 to the operating frequency; the capacitance values of these elements are identical due to the symmetrical arrangement.

Respective signal terminals 20 and 22 for supplying or tapping the antenna signal are provided parallel to the capacitive elements 15 and 16. The mammography antenna arrangement is suitable for circularly polarized operation as well as for array operation since the signal terminals 20 and 22 are each connected to an independent sub-antenna. In the transmission case, the two sub-antennas generate high-frequency magnetic fields $B_1$ and $B_2$ (symbolized respectively by arrows 23 and 25) in the examination space that are essentially horizontally directed and reside perpendicularly relative to one another. If the electrical transmission signals are phase-shifted by 90°, circularly polarized magnetic fields can be generated. It should be noted that each sub-antenna includes both arcuate conductor segments 6 and 8. The independence of the two sub-antennas has the effect that a signal supplied, for example, at the signal terminals 22 in fact generates a signal at the capacitive element 19 lying opposite thereto, but not at the capacitive elements 15 and 18. For improving the decoupling of the sub-antennas and for balancing, the conductor segments 6 and 8 can additionally be electrically connected to one another in the intersection 21 with the symmetry axis 14.

Figure 2:
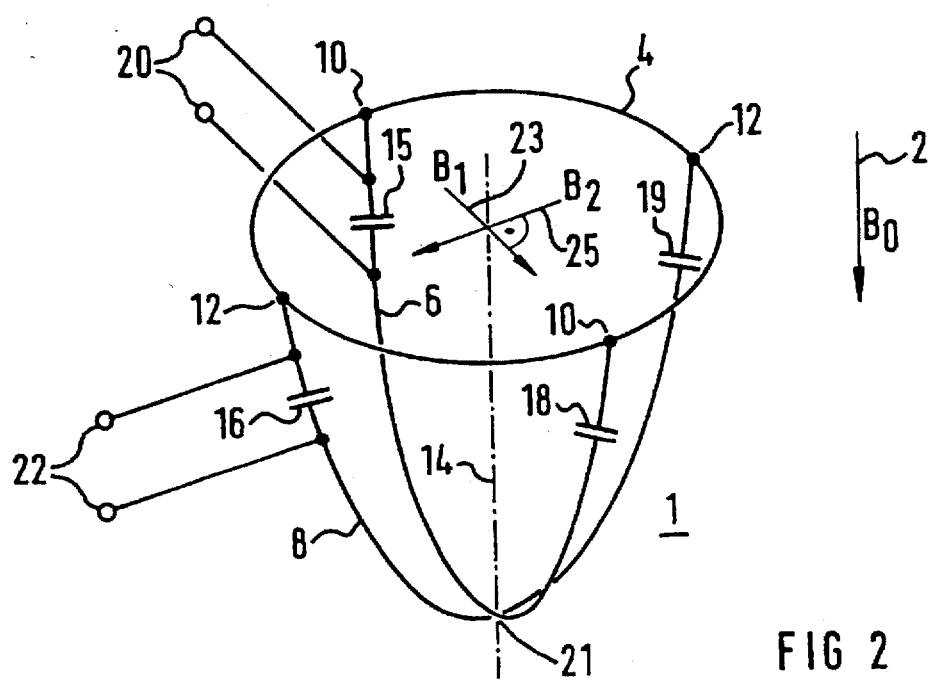
FIG. 2 illustrates a modification of the mammography antenna arrangement according to FIG. 1.

The antenna arrangement 1 of FIG. 2 differs from the antenna arrangement 1 of FIG. 1 in that the capacitive elements 15, 16, 18 and 19 are not inserted into the conductor arrangement 4, but instead are connected into the conductor segments 6 and 8 in the proximity of the connecting locations 10 and 12. The independent sub-antennas are respectively formed by arcuate conductor segment 6 and 8.

Figure 3:
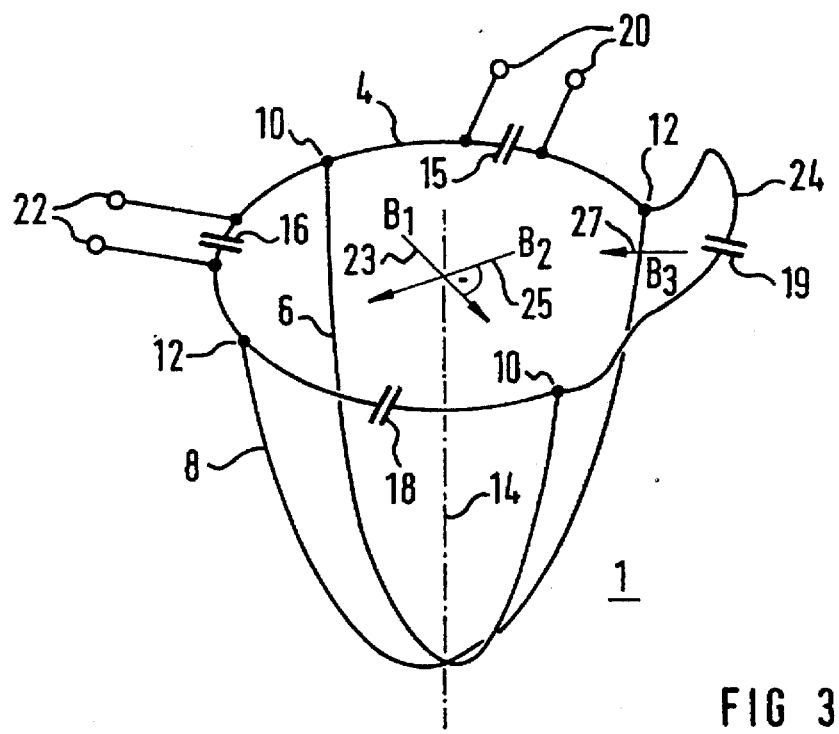
FIG. 3 illustrates a mammography antenna arrangement with enhanced sensitivity in the axillar region constructed in accordance with the principles of the present invention.

The diagnostically important axillary region can also be additionally covered with the antenna arrangement shown in FIG. 3. To that end, a part 24 of the conductor arrangement 4 is distended. This part 24 is bent out from the horizontal plane in which the receptacle opening lies, being bent upwardly away from the examination space. To the side of and above the receptacle opening, the distended part 24 thus increases the sensitivity of the antenna arrangement 1 for horizontal field components. In the transmission case, the part 24 can generate an essentially horizontally directed field $B_3$ (arrow 27) that is primarily defined by the signal at the signal terminal 22. The capacitive elements 15, 16, 18 and 19 needed for tuning and tapping signals can no longer be alike because of the now asymmetrical arrangement; in particular, the value of capacitance of the capacitive element 19 differs from the other capacitive elements 16 and 18.

Figure 4:
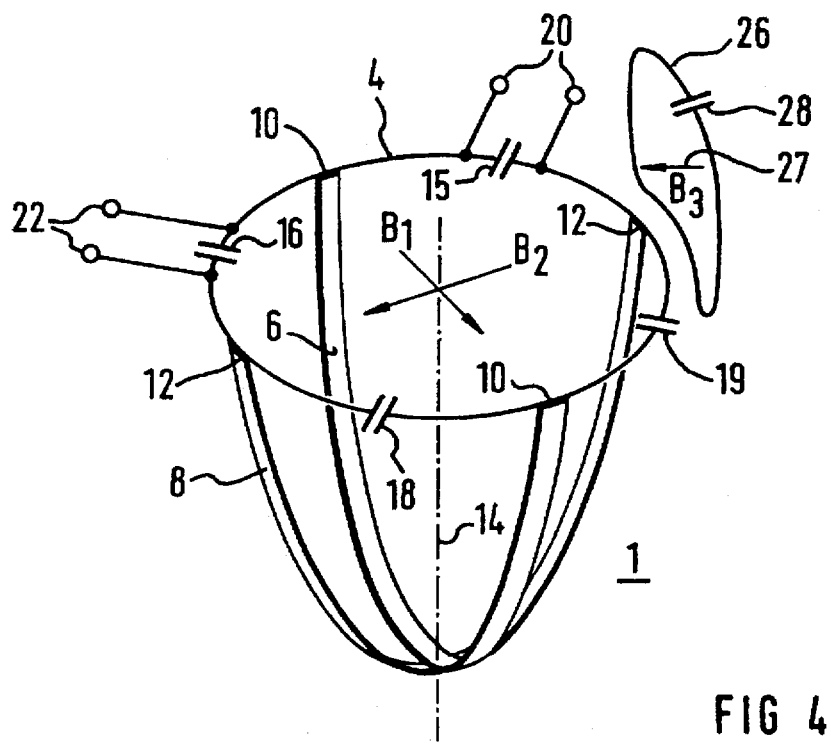
FIG. 4 illustrates a further mammography antenna arrangement constructed in accordance with the principles of the present invention with enhanced sensitivity in the axillar region.

FIG. 4 shows a further mammography antenna arrangement 1 having increased sensitivity in the axillary region. The basic structure of the antenna arrangement of FIG. 4 corresponds to the antenna arrangement of FIG. 1, however, the conductor segments 6 and 8 are fashioned ribbon-shaped in the embodiment of FIG. 4 in order to obtain improved homogeneity in the examination space. A similar field distribution to that with ribbon-shaped conductor segments 6 and 8 can also be achieved by a number of, for example, round conductors arranged in parallel. The axillary region is covered here with a further conductor loop 26 that is arranged laterally from the receptacle opening in an essentially vertical direction. Although the position of the conductor loop 26 is predetermined by the anatomy, care should be exercised to see that the sensitivity characteristic—indicated by the arrow 27 for the field direction of $B_3$—proceeds primarily horizontally. A capacitive element 28 for tuning and for tapping signals is located in the conductor loop 26.

Figure 5:
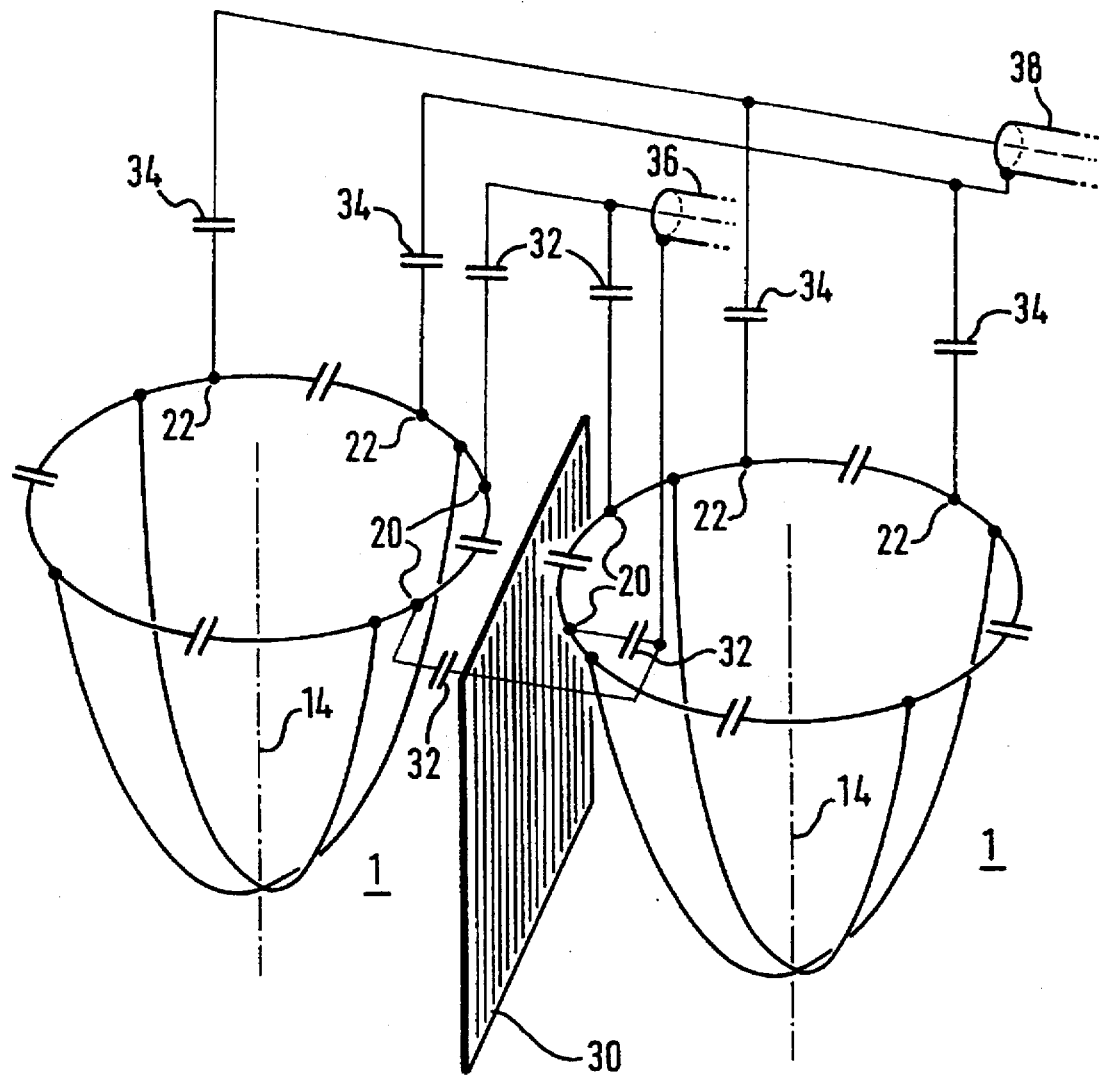
FIG. 5 illustrates a mammography antenna system having two individual antenna arrangement arranged next to one another constructed in accordance with the principles of the present invention.

A mammography antenna system having two identical, individual antenna arrangements 1 similar to the arrangement of FIG. 1 is shown in FIG. 5. The distance between the two individual antenna arrangements 1 is determined by an average anatomy but could also be variable. A radio-frequency shield 30 that keeps a mutual influencing of the individual antenna arrangements 1 to a minimum is provided for decoupling the two, individual antenna arrangements 1. The radio-frequency shield 30 is essentially composed of a planar conductor that is slotted in order to avoid gradient eddy currents. The individual antenna arrangements 1 each have signal terminals 20 and 22 connected in parallel. To that end, the signal terminals 20 and 22 are respectively connected via further capacitive elements 32 and 34 to respective feeders 36 and 38. A separate drive of the individual antenna arrangements 1 via four leads would also be possible.

The aforementioned radio-frequency shield 30 can be omitted if the inductive coupling of the two individual antenna arrangements 1 lying next to one another is compensated by a capacitive coupling. To that end, the two individual antenna arrangements 1 can be connected to one another via compensation capacitors (not shown), preferably parallel to the two signal terminals 20 lying opposite one another.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mammography antenna arrangement for conducting a magnetic resonance examination of a female breast comprising:

first and second arcuate conductors, each arcuate conductor having ends and a zenith between said ends;

a further conductor, said further conductor forming a closed circuit and defining a receptacle opening, said ends of said first and second arcuate conductors being electrically connected to said further conductor and adapted to receive a female breast when inserted in said receptacle opening, said first and second arcuate conductors being connected to said further conductor at respective junctions successively disposed along said further conductor with said arcuate conductors respectively disposed in different planes, said planes being disposed perpendicularly to each other, said arcuate conductors being identical and each lying symmetrical about a symmetry axis, said arcuate conductors, being connected to said further conductor with their respective symmetry axes coinciding;

a plurality of capacitors connected in said further conductor with at least one capacitor disposed between each pair of successive junctions;

a first signal terminal connected across a first of said capacitors; and a second signal terminal connected across a second of said capacitors, said first and second capacitors sharing a common one of said junctions and said first and second signal terminals being decoupled from each other.

2. A mammography antenna arrangement as claimed in claim 1 wherein said arcuate conductors are connected to said further conductor with said arcuate conductors overlapping at a location intersecting the coinciding symmetry axes.

3. A mammography antenna arrangement as claimed in claim 1 wherein said arcuate conductors comprise ribbon conductors.

4. A mammography antenna arrangement as claimed in claim 1 wherein said further conductor is at least partially circular.

5. A mammography antenna arrangement as claimed in claim 1 wherein said further conductor is at least partially disposed in a plane.

6. A mammography antenna arrangement as claimed in claim 1 wherein said further conductor and said arcuate conductors, in combination, form an examination space communicating with said receptacle opening matched to the anatomy of an average female breast.

7. A mammography antenna arrangement as claimed in claim 1 wherein said further conductor comprises a distended portion.

8. A mammography antenna arrangement as claimed in claim 7 wherein said arcuate conductors and said further conductor, in combination, form an examination space communicating with said receptacle opening, and wherein said distended portion of said further conductor is disposed laterally from said receptacle opening and facing away from said examination space.

9. A mammography antenna arrangement as claimed in claim 1 wherein said arcuate conductors and said further conductor, in combination, form an examination space communicating with said receptacle opening, and said mammography antenna arrangement further comprising a conductor loop disposed laterally from said receptacle opening and facing away from said examination space.

10. A mammography antenna arrangement as claimed in claim 1 wherein said further conductor, said arcuate conductors, said capacitors and said first and second signal terminals comprise a first antenna assembly, and said antenna arrangement further comprising a second antenna assembly, identical to said first antenna assembly and disposed next to said first antenna assembly, and a radio-frequency shield disposed between said first and second antenna assemblies.

11. A mammography antenna arrangement for conducting a magnetic resonance examination of a female breast comprising:

first and second arcuate conductors, each arcuate conductor having ends and a zenith between said ends;

a further conductor, said further conductor forming a closed circuit and defining a receptacle opening, said ends of said first and second arcuate conductors being electrically connected to said further conductor and adapted to receive a female breast when inserted in said receptacle opening, said first and second arcuate conductors being connected to said further conductor at respective junctions successively disposed along said further conductor with said arcuate conductors respectively disposed in different planes, said planes being disposed perpendicularly to each other, said arcuate conductors being identical and each being symmetrical about a symmetry axis, said arcuate conductors being connected to said further conductor with their respective symmetry axes coinciding;

a plurality of capacitors respectively connected in said first and second arcuate conductors, with at least one capacitor being connected in each arcuate conductor between a junction of that arcuate conductor with said further conductor and the zenith of that arcuate conductor;

a first signal terminal connected across a first of said capacitors; and a second signal terminal connected across a second of said capacitors and said first and second signal terminals being decoupled from each other.

12. A mammography antenna arrangement as claimed in claim 11 wherein said arcuate conductors are connected to said further conductor with said arcuate conductors overlapping at a location intersecting the coinciding symmetry axes.

13. A mammography antenna arrangement as claimed in claim 11 wherein said arcuate conductors comprise ribbon conductors.

14. A mammography antenna arrangement as claimed in claim 11 wherein said further conductor is at least partially circular.

15. A mammography antenna arrangement as claimed in claim 11 wherein said further conductor is at least partially disposed in a plane.

16. A mammography antenna arrangement as claimed in claim 11 wherein said further conductor and said arcuate conductors, in combination, form an examination space communicating with said receptacle opening matched to the anatomy of an average female breast.

17. A mammography antenna arrangement as claimed in claim 11 wherein said further conductor comprises a distended portion.

18. A mammography antenna arrangement as claimed in claim 17 wherein said arcuate conductors and said further conductor, in combination, form an examination space communicating with said receptacle opening, and wherein said distended portion of said further conductor is disposed laterally from said receptacle opening and facing away from said examination space.

19. A mammography antenna arrangement as claimed in claim 11 wherein said arcuate conductors and said further conductor, in combination, form an examination space communicating with said receptacle opening, and said antenna arrangement further comprising a conductor loop disposed laterally from said receptacle opening and facing away from said examination space.

20. A mammography antenna arrangement as claimed in claim 11 wherein said further conductor, said arcuate conductors, said capacitors and said first and second signal terminals comprise a first antenna assembly, and said antenna arrangement further comprising a second antenna assembly, identical to said first antenna assembly and disposed next to said first antenna assembly, and a radio-frequency shield disposed between said first and second antenna assemblies.

* * * * *